United States Patent [19]

Matsutani

[11] Patent Number: 4,611,509

[45] Date of Patent: Sep. 16, 1986

[54] METHOD OF MANUFACTURING A DENTAL ROOT CANAL CUTTING TOOL AND APPARATUS THEREFOR

[75] Inventor: Kanji Matsutani, Takanezawa, Japan

[73] Assignee: Matsutani Seisakusho, Japan

[21] Appl. No.: 657,392

[22] Filed: Oct. 3, 1984

[30] Foreign Application Priority Data

Oct. 6, 1983 [JP] Japan ................ 58-185962

[51] Int. Cl.⁴ .................... B24B 19/02; B24B 3/24
[52] U.S. Cl. .................... 76/24 R; 76/101 D; 51/95 R; 51/288
[58] Field of Search .......... 51/95 R, 95 LH, 95 WH, 51/95 TH, 288; 76/101 D, 101 R, 5 R, 108 R, 12, 24 R

[56] References Cited

U.S. PATENT DOCUMENTS 3,561,171  2/1971  Van Vleet et al. .............. 51/288

FOREIGN PATENT DOCUMENTS 2040743   9/1981  United Kingdom ........... 51/95 R
305039    3/1970  U.S.S.R. ...................... 51/288
697302   11/1979  U.S.S.R. ...................... 51/95 H
768604   10/1980  U.S.S.R. ...................... 51/95 LH Primary Examiner—Roscoe V. Parker
Attorney, Agent, or Firm—Basile, Weintraub & Hanlon

[57] ABSTRACT

A dental root canal cutting tool is formed by mounting a wire rod (3) onto a chuck-head (5). The chuck-head (5) variably rotates and advances the wire rod (3) into a guide (6) having a guide hole (7). A whetstone (9) is disposed proximate the outlet of the guide hole (7) for grinding the wire rod (3) with a taper-like shape. A space exists between the cutting edge of the whetstone (9) and the axial center of the guide hole, which varies in response to the advance of the wire rod.

2 Claims, 12 Drawing Figures

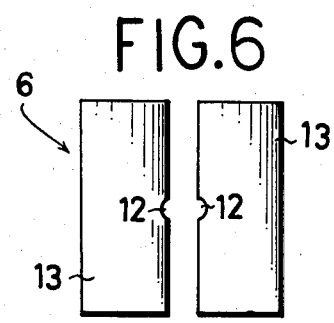
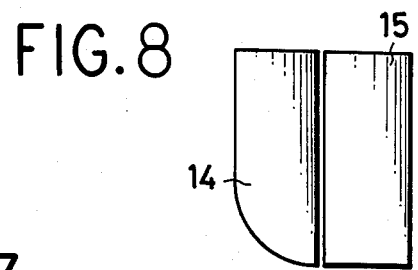
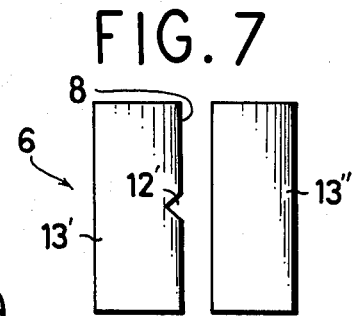
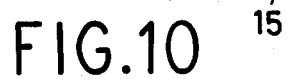
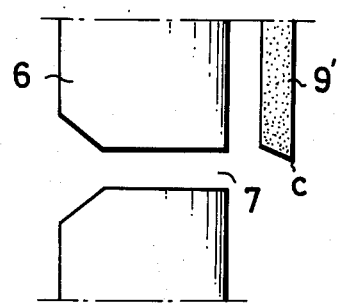
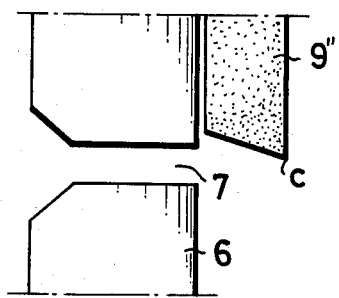
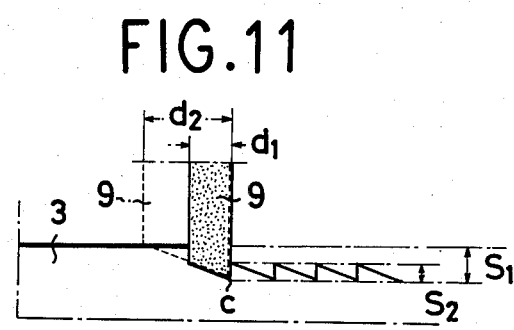
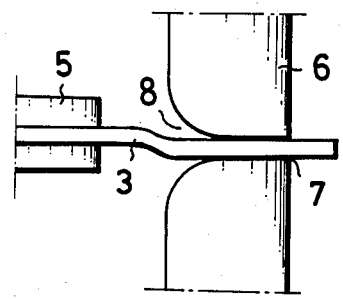

METHOD OF MANUFACTURING A DENTAL ROOT CANAL CUTTING TOOL AND APPARATUS THEREFOR

BACKGROUND OF THE INVENTION

1. Field of the Invention

The present invention relates to a method for manufacturing an H file dental root canal cutting tool and apparatus therefor.

2. Prior Art

Reamer and K file dental root canal cutting tools are manufactured by twisting a rod, which has previously been formed to a triangular or square cross-section. On the contrary, in an H file, according to the prior art, an extreme thin edge is formed on the outer environmental surface thereof. This is achieved by grinding a thin wire rod having a tip-diameter of 0.08 mm into a spiral shape, from the beginning, using a drill, a spiral end mill and the like. The 0.08 mm thickness is similar to the thickness of a hair. An edge is made by grinding and forming a spiral groove on the surface of this extremely thin wire rod. Additionally, this spiral shaped edge must be formed along a length, in the range of 16 mm, in a taper which is prescribed, usually, for example, at two-hundred mm. This is a very small and extremely difficult working range. This creates the possibility of producing articles of interior quality, which does occur frequently, and requires extreme skill by a manufacturer.

Further difficult problems in the manufacture of an H file by means of a drill, end mill, etc, as mentioned above, are as follows:

(a) the fact that a taper is in existence;
(b) the fact that the twisted angle is large;
(c) the fact that the H file must be formed with a metallic wire rod having soft, non-rigid properties because of the potential for fragmentation;
(d) the fact that austenitic stainless steel is commonly used, in order to prevent an occurrence of rust, but this material is extremely difficult to grind;
(e) the fact that the H file must be produced at a price of several tenths or several hundredths of the price of the drill and the like because the H file is used only once and, then, thrown away.

Ordinarily, and as shown in FIGS. 1 and 2, hitherto, the grinding of an H file was accomplished by the following procedure: a wire rod 3' is placed on a U-shaped or V-shaped groove 2' which is mounted on a guide 1', in the same manner as a drill. Grinding is performed by advancing the wire rod 3' while it is revolved. Simultaneously, a thin whetstone 4' is set up, with a fixed twisted angle $\theta$, against the groove 2' and is pressed against the wire rod 3'. When an H file is ground by this method, the H file is ground thinner than the diameter of the wire rod 3', with a taper of about two-hundredths mm, which of course, may differ because of drill variations and the like. Consequently, the ground portion becomes unstable, by floating in the groove 2', and has poor grinding precision. Likewise, a force toward the right-angled axial direction created by the revolving of the whetstone 4' in order that the twist or twisted angle $\theta$, of the whetstone 4', can approach a right angle, and, generally, at an angle of 45° to 65° exerts a large influence on the ground portion. Consequently, there is the danger that the wire rod 3' may jump out from the groove 2' at the time of grinding when the wire rod 3' is in an unstable state. Likewise, even if the wire rod 3' does not jump out of the groove, variations in grinding, caused by a run phenomenon on the side wall of the groove, may be produced by the wire rod pressing against the side wall of the groove with a large force.

Furthermore, as mentioned above, in order that the floating of the ground portion of the wire rod 3' in the groove 2' may lessen, a spiral grinding trial is performed after the wire rod 3' is previously ground to a taper-like shape. But, the groove 2' becomes shallow, and the depth of the groove 2' must be adjusted to a minimum diameter of the wire rod 3'. If the wire rod 3' jumps up from the groove 2', when grinding, under the influence of the fact that the twisted angle $\theta$ of the whetstone 4' is large, there is created a defect in that the edge and its tip are damaged. This is because the ground edge touches the groove 2', and because the extremely thin wire rod is, ordinarily, made of a soft material.

The present invention breaks down the fundamental conventional idea that it is natural that precision be somewhat poor because a low-priced edge tool is involved. Likewise, the present invention provides an entirely new technique which has been developed in view of the conventional defects mentioned above.

OBJECT OF THE INVENTION

Accordingly, it is an object of the present invention to provide a technique wherein a wire rod is ground, while supporting all environmental directions, without placing the wire rod in a groove, as is usually the case, in grinding a dental H file having a tip-diameter of more than 0.08 mm.

SUMMARY OF THE INVENTION

The present invention provides a method for manufacturing a dental root canal cutting tool and apparatus therefor, characterized in that a wire rod is inserted into a guide hole having an inside diameter capable of supporting the wire rod, while the wire rod is revolved and advanced. The revolved and advanced wire rod is ground by a whetstone having a fixed edge disposed at the outlet of the guide hole. A space exists between the axial center of the guide hole and the edge of the whetstone and is varied, gradually, in response to the advance of the wire rod. Likewise, the advancing volume per revolution of the wire rod is, also, varied.

For a more complete understanding of the present invention reference is made to the following detailed description and accompanying drawing. In the drawing like reference characters refer to like parts throughout the several views, in which:

BRIEF DESCRIPTION OF THE DRAWING

FIG. 6 is a front elevational view of an alternate guide used in the practice of the present invention;

FIG. 7 is a front elevational view of another embodiment of a guide used in the practice of the present invention;

FIG. 8 is a front elevational view of a further embodiment of a guide used in accordance with the present invention;

FIG. 9 is a fragmentary, side elevational view depicting the positional relationship between the guide and the whetstone and the thickness of the whetstone;

FIG. 10 is a further fragmentary, side elevational view depicting an alternate positional relationship between the guide and the whetstone and thickness of the whetstone;

FIG. 11 is a still further fragmentary, side elevational view depicting a further positional relationship between the guide and the whetstone and thickness of the whetstone; and FIG. 12 is a fragmentary view showing the position between the wire rod and the guide hole when the guide hole gets out of position.

DETAILED DESCRIPTION OF THE PREFERRED EMBODIMENTS

Figure 1:
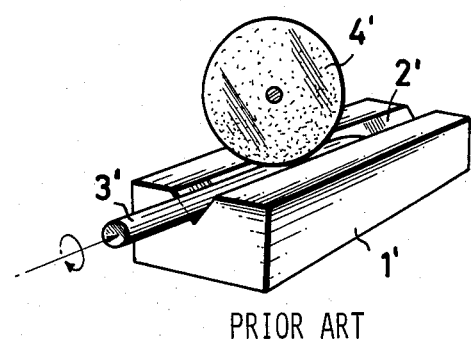
FIG. 1 is a perspective view of a prior art grinding method for an H file and its apparatus.
Figure 2:
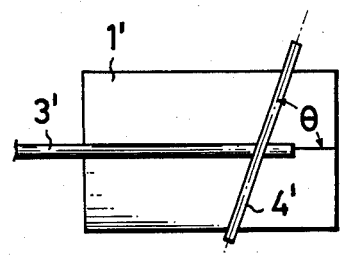
FIG. 2 is a top plan view of the prior art grinding method for an H file and its apparatus.
Figure 3:
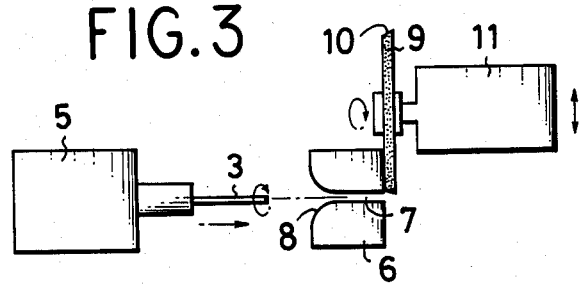
FIG. 3 is a side elevational view of a grinding method and apparatus therefor in accordance with the present invention.

Referring now to the drawing and, in particular, FIG. 3, there is provided a chuck-head 5 capable of grasping and revolving a wire rod 3 which has a diameter of 0.4–1.6 mm and which is cut with a fixed length. The chuck-head 5 is constructed such that the grasped wire rod 3 may be advanced, while revolving, by a motor (not shown). The advancement of the wire rod 3 varies according to the advanced position of the chuck-head 5.

The front of the chuck-head 5 is provided with a guide 6 formed of cemented carbide, ceramic or diamond. The guide 6 has a guide hole 7 having an inside diameter which is larger than the diameter of the wire rod 3, e.g. on the order of 0.005–0.02 mm. The guide hole 7 is on an extension line coaxial with the wire rod 3. The guide hole 7 penetrates and is perforated in the guide 6. The guide hole 7 supports the wire rod 3 when the wire rod 3 is inserted thereinto. The guide 6 has a trumpet-like portion 8. The portion 8 is formed so as to enable easy insertion of the wire rod 3 at the inlet portion of the guide hole 7.

A thin whetstone 9, having a thickness of about 2.5 mm, is disposed close to the front or outlet of the guide 6 and is arranged with a twisted angle $\theta$ relative to an axial center of the guide hole. The whetstone 9 has an edge-tip 10 which is formed with the shape of the Japanese FIG. 8. The whetstone 9 grinds the wire rod 3 by either a wet process or a dry process in order to form a spiral shape on the rod 3. The wire rod 3 is rotatingly advanced out from the guide hole 7 by revolving said wire rod 3 by means of a motor 11, which rotates the whetstone 9.

The whetstone 9 is slidably mounted, to be positioned between the upper and lower directions in FIG. 3, and is constructed such that a space between the axial center of the guide hole 7 and the edge-tip 10 of the whetstone 9 may be varied.

Figure 4:
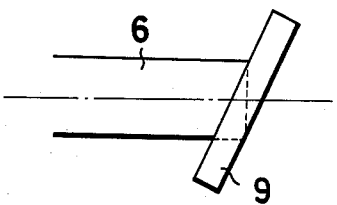
FIG. 4 is a fragmentary view of a guide and whetstone used in the practice of the present invention.

Further, in bringing the whetstone 9 to the front or outlet of the guide 6 with the twisted angle $\theta$ (the twisted angle $\theta$ is an inclined angle, in the right-angled direction of FIG. 3) the shape in which the whetstone 9 cuts shavings off, in response to the twisted angle $\theta$, is, preferably, that shown in FIG. 4. It is preferred that the whetstone 9 not touch the opposite side of the guide 6.

Figure 5:
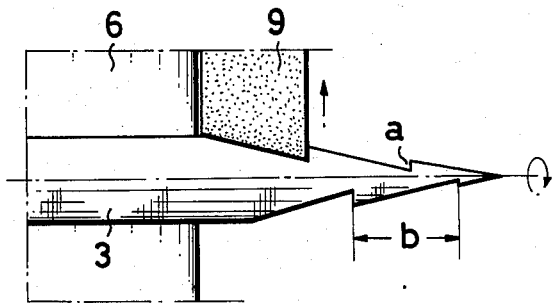
FIG. 5 is a fragmentary view of the grinding operation in accordance with the present invention.

Referring now to the method in accordance with the present invention; first the wire rod 3 is grasped by the chuck-head 5; then, the wire rod 3 is advanced, while revolving, in the direction of the arrow in FIG. 3; the wire rod 3 is inserted into the guide hole 7 perforated into the guide 6. As noted, all environmental directions of the wire rod 3 are supported by the inside environment of the guide hole 7. The wire rod 3 coming out of the guide hole 7 is ground by the whetstone 9, as shown in FIG. 5. It is possible to form a tapered spiral groove in the wire rod 3 by gradually moving the whetstone 9 upward at the time of the grinding.

Furthermore, and as shown in FIG. 5, a pitch b of the spiral groove can be formed by gradually enlarging the advanced volume, per revolution of the wire rod 3, caused by the chuck-head 5. Since the diameter of the edge enlarges in proportion to the portion which the pitch is enlarged, even if the upper movement of the whetstone 9 is not performed, the wire rod 3 can be formed with the tapering taper-like edge, as well as the spiral groove having a large groove-pitch b, in the root of the wire rod 3.

In other words, by the combination of the upper movement of the whetstone 9 and the variation in the advanced volume per revolution of the wire rod 3, it is possible that an H file having a fixed taper and a fixed pitch can be manufactured.

In FIG. 6, there is shown an alternate embodiment of the guide. According to this embodiment, the guide hole 7 in the guide 6 is formed by two symmetrical guide pieces 13,13, each having a semicircular grooved way 12 formed therein. The guide 6 is formed by joining the guide pieces 13,13 together in order that the left grooved way 12 coincides with the right grooved way 12.

FIG. 7 depicts a further embodiment of the guide 6. According to this embodiment, the guide 6 is constituted by joining, respectively, a guide piece 13', having a square-shaped grooved way 12' in the side with a guide piece 13'' having a non-grooved way. Further, the trumpet-like portion 8 formed at the inlet portion of the guide hole 7 is incorporated into the guide pieces 13' and 13''. Alternatively, and as shown in FIG. 8, the trumpet-like portion may be formed by joining together a trumpet-like piece 14 and a straight piece 15, the separate pieces 14,14 and 15,15 cooperating to define the guide 6.

As noted, it is desirable that the whetstone 9 be close to the front or outlet of the guide 6. When the whetstone separates from the front of the guide 6, as shown in FIG. 9, the wire rod 3 may bend with the grinding force caused by the whetstone 9; or the grinding precision may become poor. Furthermore, even if the whetstone 9 is close to the front of the guide 6, when a thick whetstone 9'' (FIG. 10) is used, the tip portion C of the whetstone 9'' becomes distant from the front of the guide 6. This is equal to the situation where the whetstone is far away from the front of the guide. Therefore, it is desirable that the thickness of the whetstone 9 be thin. But, meanwhile, during the grinding of the H file, the tip portion C of the whetstone is easily worn away. Therefore, it is desirable to thicken the whetstone 9 to some extent in order to lessen this abrasion.

The relationship between thickness and abrasion of the whetstone 9 is shown in FIG. 11. As shown in FIG. 11, a scraped into-volume of the tip portion C of the whetstone 9 is denoted as S and has a thickness $d_1$. Contrariwise, the scraped into-volume of the tip portion C lessens to $S_2$ when the thickness of the whetstone is enlarged to $D_2$, or when the degree of abrasion in the tip portion C lessens the tip that much. Therefore, considering both issues of grinding precision and the degree of abrasion of the tip of the whetstone 9, the thickness of the whetstone 9 should be greater than P sin θ wherein the maximum pitch of an H file is P and the twisted angle is θ. The thickness of whetstone 9, while being more than P sin θ, should not be much above this thickness. Likewise, and as noted, it is desirable that the whetstone 9 be arranged closed to the front of the guide 6.

Furthermore, when the space between the axial center of the guide hole 7 and the tip portion 10 of the whetstone 9 is varied, the whetstone 9, being slid by this time, it is preferable to slide the guide 6 contrariwise, or that both sides of the guide 6 and the whetstone 9 be slid.

As shown in FIG. 12, when the guide 6 is slid, the relative position between the axial center of the wire rod 3 and, the guide hole 7 slips out of place a little, in relationship to the chuck-head 5. This discrepancy is, at most, about one-half of the diameter of the wire rod 3, which is minute. Since the wire rod 3 is fully flexible, in order that the wire rod may be thin and long, the wire rod 3 is modified forcibly by the trumpet-like portion 8 of the guide 6. Therefore, when the wire rod 3 is conducted to the guide hole 7, no problem exists due to the relative displacement. Indeed, it is preferable that a discrepancy exist between the centers of the wire rod 3 and the guide hole 7 to some extent. Then the clearance between the wire rod 3 and the guide hole 7, caused by the fact that the diameter of the guide hole 7 is about at 0.005–0.02 mm larger than the diameter of the wire rod 3, can be reduced. This clearance reduction results in improved grinding precision. Therefore, during grinding, a discrepancy between the center of the wire rod 3 and guide hole is created when the guide 6 moves to the side of the whetstone 9. When the guide 6 separates from the whetstone 9, at final grinding, and the guide 6 is pulled back from the whetstone 9, by coinciding the center of the guide hole 7 with the wire rod 3, the grinding precision is improved. Likewise, it is possible that the ground edge be pulled back without touching the guide hole 7, entirely.

It is, also, possible to send out the ground edge ahead on the wire rod 3, as is, without pulling the edge back after grinding.

Although the present invention has been described with respect to a one piece whetstone 9, it is possible to grind a two-way spiral edge by arranging two whetstones for back and forth movement. Further, it may be possible to grind a three way-spiral edge by properly arranging three whetstones.

In the apparatus of the present invention, the guide is provided with the guide hole; the wire rod is inserted in the guide hole, and the apparatus supports the wire rod. If an H file is manufactured by the present apparatus, all directional environment of the wire rod 3 is supported by the guide hole 7.

Consequently, since the wire rod can be stably supported, it is possible to improve the grinding precision. Further, during grinding, a large resisting force exists against the grinding force of the rightangled direction of the axis of the wire rod, and since the grinding is performed just after the wire rod is projected from the guide hole, the edge portion, after grinding, does not come into contact with the guide. Consequently, it is possible to grind the wire rod without damaging the edge entirely. Furthermore, even if the position between the wire rod and the guide hole slips out of place somewhat, it is possible to guide the wire rod, within the guide hole, by forcibly modifying the position of the trumpet-like portion of the inlet portion of the guide hole. As noted, there is an advantage in a certain measure of positional discrepancy, as it improves grinding precision.

In order that the apparatus perform so as to vary, in turn, the distance between the axial center of the guide hole and the tip portion of the whetstone, as well as to vary, gradually, the advancing volume per revolution of the wire rod, the wire rod is ground with a taper-like shape. Simultaneously with the formation of the taper, it is possible to grind spiral grooves having varied pitches, and it is possible to lessen the manufacturing process of an H file.

As discussed hereinabove, the present invention permits the wire rod to be supported by the inner environmental surface of the guide hole by inserting the wire rod thereinto. But, since the wire rod is advanced per revolution thereof, the wire rod can be inserted smoothly into the guide hole, even if the diameter of the wire rod is considerably close to the inside diameter of the guide hole.

It is, also, possible, in accordance herewith, that the wire rod be pulled out very smoothly from the guide hole since the diameter of the wire rod may be made thinner than the diameter before grinding, and, then, when the wire rod is pulled out, after grinding, it may be ground with the taper-like shape.

Further, it is possible that the present invention be utilized for the manufacture of a dental root canal cutting tool as well as a dental rood canal filling tool. This is achieved by forming an oppositely directed groove.

Having, thus, described the invention, what is claimed is:

1. A method for manufacturing a dental root canal cutting tool comprising the steps of:
   inserting a wire rod into a guide hole having a slightly larger inside diameter than the diameter of the wire rod;
   revolving and advancing the wire rod at a fixed rate while the wire rod is being inserted into the guide hole;
   supporting the wire rod in all environmental directions by the inside environment of the guide hole;
   grinding the wire rod by a thin whetstone having a fixed tip at an edge thereof just after the wire rod penetrates and exits the guide hole; and
   gradually varying the space between an axial center of the guide hole and the tip of the whetstone in response to the advance of the wire rod.

2. An apparatus for manufacturing a dental root canal cutting tool from a wire rod, comprising:
   (a) a chuck-head for grasping the wire rod, the chuck-head being formed so as to revolve and advance said wire rod;
   (b) a guide having a guide hole formed therein, the guide hole having a slightly larger inside diameter than the diameter of said wire rod, the guide being positioned in the front of said chuck-head; and
   (c) a thin whetstone having a fixed tip at an edge thereof, said whetstone being arranged with a fixed twisted angle relative to the axial center of said guide hole, the whetstone being arranged closely to the front of said guide, and wherein the distance between the axial center of said guide hole and the tip of the edge of said whetstone varies responsively with the advance of said chuck-head.

* * * * *